US008697931B2

(12) United States Patent
Suutari et al.

(10) Patent No.: US 8,697,931 B2
(45) Date of Patent: Apr. 15, 2014

(54) BANDAGING ELEMENT OF FIRST AID BANDAGE AND FIRST AID BANDAGE

(76) Inventors: Janne Suutari, Kajaani (FI); Markku Liuke, Helsinki (FI)

(*) Notice: Subject to any disclaimer, the term of this patent is extended or adjusted under 35 U.S.C. 154(b) by 471 days.

(21) Appl. No.: 12/988,032

(22) PCT Filed: Mar. 25, 2009

(86) PCT No.: PCT/FI2009/050228
§ 371 (c)(1),
(2), (4) Date: Dec. 29, 2010

(87) PCT Pub. No.: WO2009/127777
PCT Pub. Date: Oct. 22, 2009

(65) Prior Publication Data
US 2011/0092873 A1    Apr. 21, 2011

(30) Foreign Application Priority Data
Apr. 17, 2008    (FI) .................................... 20085322

(51) Int. Cl.
*A61F 5/00* (2006.01)
*A61F 13/00* (2006.01)

(52) U.S. Cl.
USPC .............................................. 602/53; 602/42

(58) Field of Classification Search
USPC ................. 602/48–53, 56–59, 72, 61–64; 604/304–380; 606/203–204
See application file for complete search history.

(56) References Cited

U.S. PATENT DOCUMENTS

| 5,628,723 | A | 5/1997 | Grau |
|---|---|---|---|
| 6,441,265 | B1 * | 8/2002 | Chan ................................ 602/53 |
| 6,593,508 | B1 | 7/2003 | Harder |
| 6,936,018 | B2 * | 8/2005 | Chalek ............................... 602/2 |
| 7,652,190 | B2 * | 1/2010 | Johnson ........................... 602/48 |
| 2007/0185428 | A1 | 8/2007 | Harder |

FOREIGN PATENT DOCUMENTS

| CN | 200984285 Y | 12/2007 |
|---|---|---|
| WO | 2007043749 A1 | 4/2007 |

* cited by examiner

*Primary Examiner* — Patricia Bianco
*Assistant Examiner* — Ophelia A Hawthorne
(74) *Attorney, Agent, or Firm* — Volpe and Koenig, P.C.

(57) ABSTRACT

A first aid bandage includes bandaging material, a dressing pad and a bandaging element. The dressing pad is attached underneath the bandaging element. The bandaging material is attached to the bandaging element. The bandaging element has been rolled up so that there is a rolled-up portion and a straight portion in the bandaging element. The rolling has been done so that the rolled-up portion can be rolled up over the straight portion, whereby the bandaging element is put in a state of tension. There is an opening arrangement in the rolled-up portion of the bandaging element, in which opening arrangement there are guiding structures. The bandaging material is arranged to fit into the opening arrangement so that a part of the bandaging material is under the guiding structures.

12 Claims, 6 Drawing Sheets

BANDAGING ELEMENT OF FIRST AID BANDAGE AND FIRST AID BANDAGE

FIELD OF INVENTION

Figure 1:
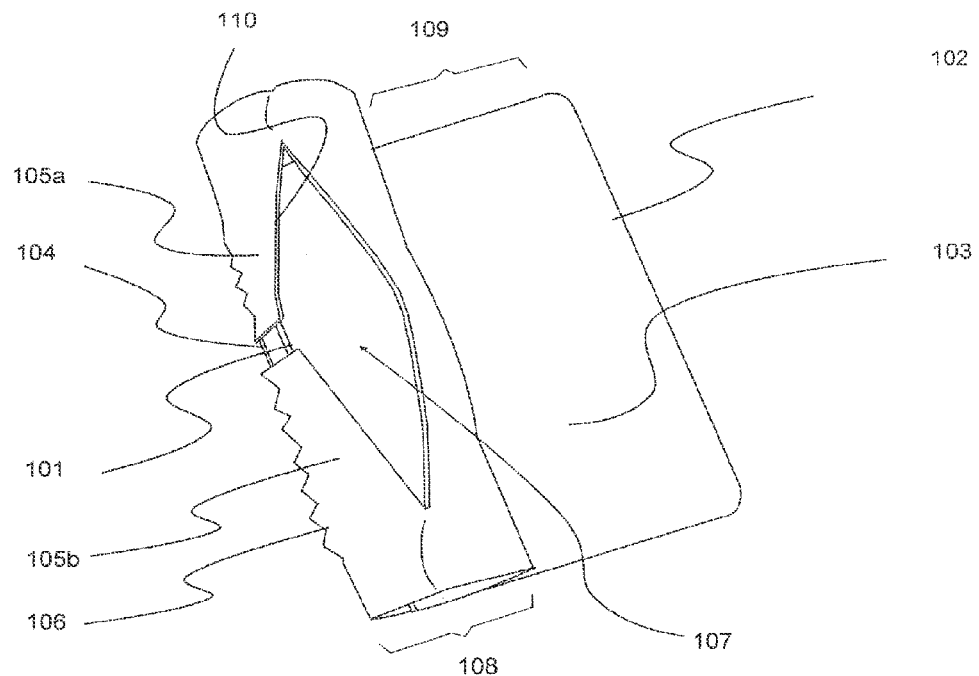

Invention relates to a bandaging element of a first aid bandage, which element comprises a support part of a dressing pad and a compression part, and to a first aid bandage, which comprises bandaging material, a dressing pad, and the bandaging element and dressing pad are attached to the support part of the dressing pad of the bandaging element and the bandaging material is attached to the bandaging element.

BACKGROUND

It is known that a first aid bandage is used as a first aid to a bleeding wound. This bandage consists of a dressing pad that is placed against the wound, flexible or inflexible bandaging material and a compression part. The compression part is placed under the first layer of the bandage made with the bandaging material. The bandage made with the bandaging material applies pressure on the compression part and this causes pressure to the wound and its immediate vicinity. The pressure blocks the injured veins and thus stops or controls the bleeding. The compression part can be any applicable element with a suitable form and material. The bandaging material is long enough that it can be wrapped several times around an injured extremity or body part to apply pressure on the compression part and protect the wounded area. The bandage made with the bandaging material has to be fastened to its place by tying, with tape, Velcro, hooks, pins or other corresponding means.

In the wound bandaging method described a separate dressing pad has to be placed against the wound and a separate compression element has to be placed inside the bandage. The method is slow and requires favourable working conditions and experience from the person placing the bandage. Furthermore separate components bring packing and unpacking problems.

The problems mentioned are aspired to solve in patent publication US5628723. It describes a first aid bandage, which consists of one piece. It comprises a dressing pad, compression mechanism and bandaging material. The compression mechanism presented by the publication is however quite difficult to use and requires precision and focus from its user. The first aid bandage described is also very difficult to use for independent first aid.

A one-piece first aid bandage, which is comprised of a dressing pad, tightening means and bandaging material equipped with Velcro fabric, is known in patent publication US6593508. The tightening means is a hook-like structure, around which the bandaging material is wrapped to tighten it and to cause pressure to the dressing pad. The first aid bandage described is simple to use, but the bandage can loosen very easily and the pressure caused by it is focused on a small area.

SUMMARY

An objective of the invention is to introduce a first aid bandage, with which the disadvantages and defects associated with the prior art can be significantly reduced. A further objective of the invention is to facilitate first aid given under difficult conditions.

The objectives according to the invention are achieved with a first aid bandage and a bandaging element of a first aid bandage, which are characterised in what is set forth in the independent claims. Some advantageous embodiments of the invention are presented in the dependent claims.

The bandaging element of a first aid bandage according to the invention comprises a support part of a dressing pad and a compression part. The bandaging element is substantially a planar element. It has a first end and a second end. The bandaging element has been rolled up from its first end so that the bandaging element comprises a rolled-up portion and a straight portion. This rolled-up portion is a compression part and the straight portion of the bandaging element is a support part of the dressing pad. The first end of the bandaging element is inside the rolled-up portion. The rolled-up portion forms an approximately cylindrical part. This rolling has been done so that the rolled-up portion can further be rolled up over the straight portion, whereby the bandaging element is put in a state of tension. The bandaging element tries to recover from this state of tension back into its original state, in which the bandaging element was before the rolled-up portion was rolled up over the straight portion. This direction, in which the rolled-up portion is rolled up over the straight portion to tighten the bandaging element, is the rolling direction. In the rolled-up portion there is an opening arrangement for the bandaging material to go through.

In an embodiment of a bandaging element of a first aid bandage according to the invention there are one or more guiding structures in the opening arrangement to guide the bandaging material. There is a first side and a second side in the guiding structures. The first side is closer to the first end of the bandaging element measured along the surface of the bandaging element and the second side is on the opposite side of the first side of the guiding structure. The second side of the guiding structure is shaped to catch the bandaging material. This shaping is advantageously toothing.

In a second embodiment of the bandaging element of a first aid bandage according to the invention there are two of the guiding structures and they are situated substantially on the opposite sides of the opening arrangement. The shaped second sides of the guiding structures are substantially parallel to the longitudinal axis of the rolled-up portion of the bandaging element. The guiding structures extend towards each other and there is a gap between them. The first sides of the guiding structures are at the end of the guiding structure closer to the second side than at the base of the guiding structure. Thereby the first sides of the guiding structures become oblique and they guide the bandaging material.

In a third embodiment of the bandaging element of a first aid bandage according to the invention the edge of the guiding structures on the side of the second sides is rounded so that the middle of the edge is closer to the second sides of the guiding structures than the margins of the edges. This rounded edge spreads the bandaging material going through the opening arrangement.

In an embodiment of the first aid bandage according to the invention the material of the bandaging element is plastic.

A first aid bandage according to the invention comprises bandaging material, a dressing pad and a bandaging element. The dressing pad is attached to the support part of the dressing pad of the bandaging element. The bandaging material is attached to the bandaging element. The bandaging element is attached to an end of the bandaging material so that the main part of the bandaging material is substantially on the side of the rolled-up portion of the bandaging element. In other words when the bandaging material is straightened, without being rolled, it is substantially towards the opposite direction from the rolling direction of the bandaging element.

The rolled-up portion of the bandaging element comprises an opening arrangement. This opening arrangement is for the bandaging material to go through. The bandaging material is guided and the roll-like portion is tightened with the help of it. The bandaging material turning from below the bandaging element, that is from the side where the dressing pad is attached, above it and coming from the rolling direction is arranged to fit to the opening arrangement so that a part of the bandaging material is under the guiding structures. When a force is directed at the bandaging material going through the opening arrangement from the rolling direction, substantially in the direction of the rolling direction, in other words the bandaging material is pulled more or less towards the rolling direction, the bandaging material catches the guiding structures of the opening arrangement and the shaping of their second sides. The rolled-up portion of the bandaging element can be tightened with the bandaging material caught in the guiding structures by directing force in the direction of the rolling direction with the help of bandaging material to the rolled-up portion. During the rolling the part of the bandaging element on top of the dressing pad changes its shape. This part of the bandaging element, that has changed its shape, on top of the dressing pad applies pressure to the dressing pad. The bandaging element brought into a state of tension is covered by wrapping the bandaging material several times around the object on which the bandage is placed. Then the bandaging material holds the bandaging element, which is in a state of tension, substantially in its place. The bandaging material is anchored in some suitable way. These anchoring means are adhesive labels, adhesive tape, glues, hooks, rivets, pins or the like.

When a tightened roll-like part is covered with bandaging material, a bandage is created wherein the bandaging element in a state of tension both tightens the bandage and applies pressure to the dressing pad. When such a bandage is made over the wound so that the dressing pad is against the wound to be dressed, the pressure applied by the bandaging element to the dressing pad presses the blood veins of the wounded area closed thus decreasing the bleeding.

An advantage of the invention is that it is easy to use and quick to place. It can be used by a person who has no experience in dressing wounds. It can be used under difficult conditions. It can be placed on oneself. A first aid bandage according to the invention can be placed on the wounded area with one hand.

A further advantage of the invention is that already the first layer of the bandaging material round will anchor the bandage to its place.

A further advantage of the invention is that it offers a wider area stopping the flow of blood compared to prior art. Also a greater compressive force can be applied on the bleeding area than in prior solutions.

An advantage of the invention is also that with the help of it the compression can be regulated. The invention can be used for treatment of traumas of the extremities, body and the head.

BRIEF DESCRIPTION OF THE DRAWING(S)

Figure 2:
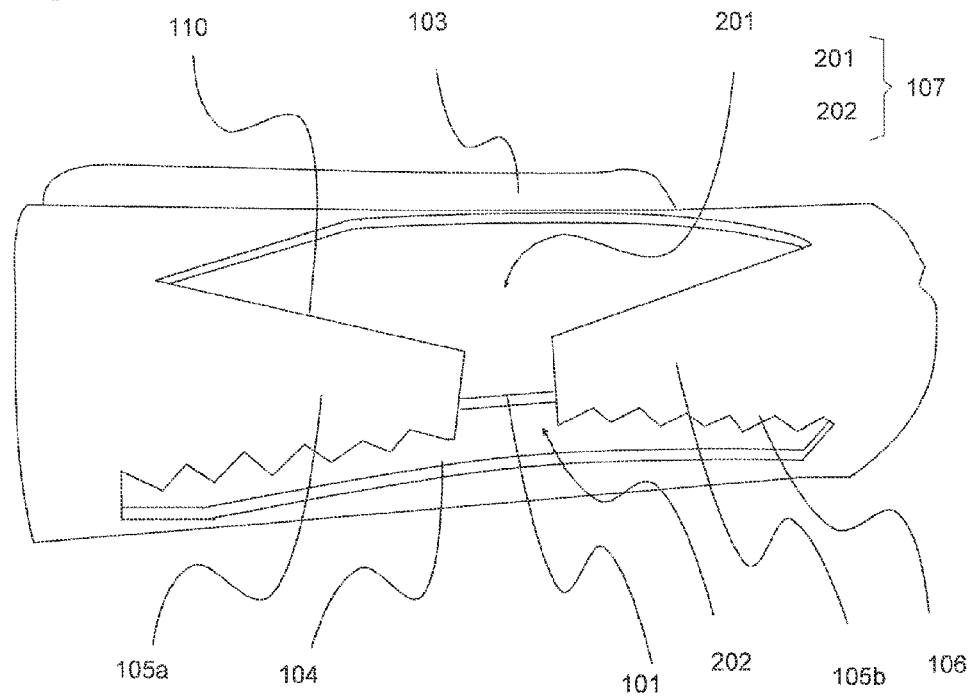
Figure 3:
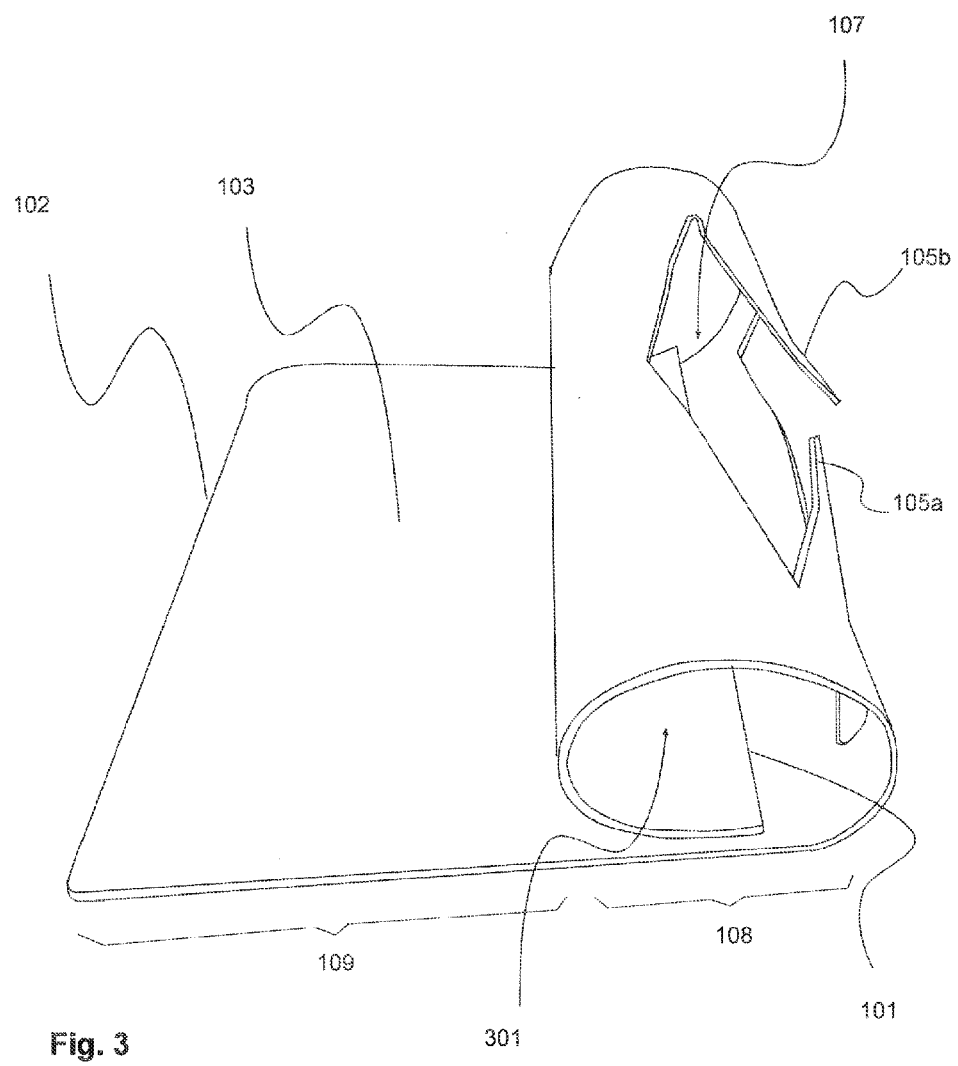
Figure 4:
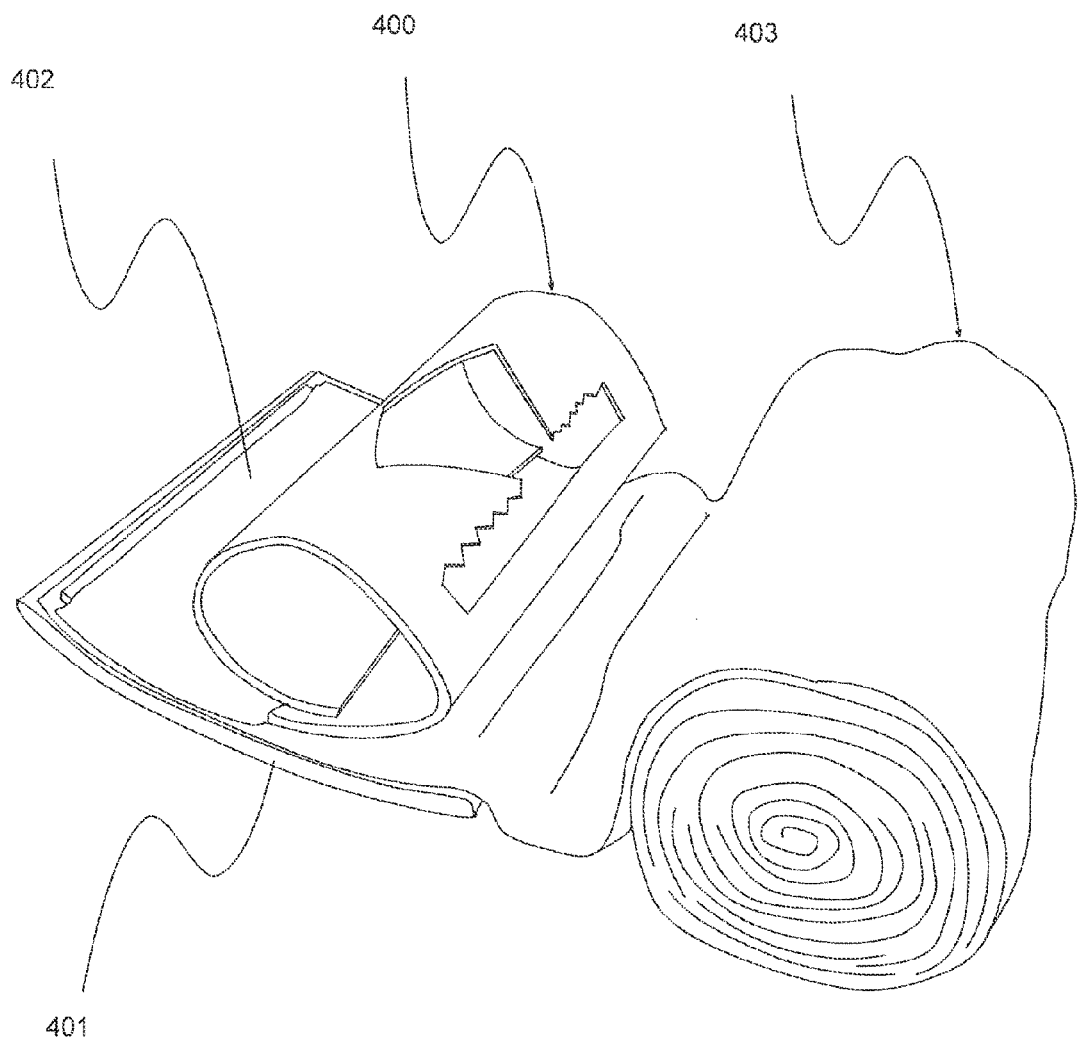

Next the invention will be described in detail. In the description reference is made to the accompanying drawings, in which FIG. 1 shows as an example a bandaging element of a first aid bandage according to the invention as seen from above, FIG. 2 shows as an example a bandaging element of a first aid bandage according to the invention as seen from the front, FIG. 3 shows as an example a bandaging element of a first aid bandage according to the invention as seen from the side, FIG. 4 shows as an example a first aid bandage according to the invention and FIGS. 5-10 show as an example the use of a first aid bandage according to the invention to dress a wound in an extremity.

DETAILED DESCRIPTION OF THE PREFERRED EMBODIMENT(S)

FIG. 1 shows as an example a bandaging element of a first aid bandage according to the invention as seen from above. The bandaging element is a laminar structure, which has an upper surface 103 and a lower surface and a first end 101 and a second end 102. Advantageously this laminar structure resembles a parallelogram. The bandaging element has a rolled-up portion 108 and a straight flat portion 109, and the end of the straight flat portion of the bandaging element is the second end 102. The rolled-up portion is formed by bending the laminar structure from its first end over itself into a roll. Then the first end 101 of the laminar structure is left inside the roll-like structure. The laminar structure has been rolled up over the upper side of the bandaging element. The direction from the rolled-up portion towards the second end of the plate structure is called the rolling direction. The lower side of the bandaging element has substantially the same form as the lower side of the straight portion of the bandaging element. The rolling of the plate has been done so that it has a tendency to return to its original rolling state, if it has been tightened by rolling it further towards the rolling direction or by opening the rolling. This rolled-up portion is made for example by casting or shaping, when the material of the laminar structure is in a mouldable state.

There is an opening arrangement 107 in the rolled-up portion of the bandaging element. The opening arrangement is an opening through the laminar structure of the bandaging element. The opening arrangement extends from that part of the rolled-up portion, which is substantially furthest away from the plane of the straight portion to that side of the rolled-up portion which is furthest away from the second end of the bandaging element. There are two guiding structures 105a and 105b in the opening arrangement. The guiding structures are elongated projections on the edges of the opening arrangement. The guiding structures are on the opposite sides of the opening arrangement and they extend towards each other. The guiding structures are substantially parallel to the longitudinal axis of the rolled-up portion. The guiding structures have two long sides: a first side 110 and a second side 106. The first side is closer to the first end 101 of the plate-like structure of the bandaging element than the second side measured along the surface of the laminar structure and the second side is further away from said first end than the first side measured along the surface of the laminar structure. The second sides 106 of the guiding structures are substantially parallel to the longitudinal axis of the rolled-up portion. These second sides are shaped to catch the bandaging material. This shaping can be a toothing. Advantageously the toothing or other shaping of the second side of the guiding structure is made so that they interfere as little as possible the movement of the bandaging material going through the opening arrangement under the guiding structures. Further their shaping enables the bandaging material to get caught when the pulling direction of the bandaging material running through the opening arrangement is changed substantially parallel to the rolling direction. The ends of the guiding structures advantageously project from the surface formed by the rolled-up portion.

FIG. 2 shows as an example a bandaging element of a first aid bandage according to the invention as seen obliquely from above towards the rolling direction. The guiding structures 105a and 105b devide the opening arrangement 107 into two parts: an upper part of the opening arrangement 201 and lower part of the opening arrangement 202. The upper part of the opening arrangement is on the side of the first sides 110 of the guiding structures and the lower part of the opening arrangement is on the side of the second sides 106 of the guiding structures. The width of the opening arrangement in both upper and lower part in the direction of the longitudinal axis of the rolled-up portion is substantially such that the bandaging material can easily be taken through the opening arrangement. Advantageously the bandaging material is brought into the opening arrangement through the upper part of the opening arrangement, is taken under the guiding structures and brought out of the opening arrangement through the lower part of the opening arrangement.

To make it easy for the bandaging material to be taken through via the opening arrangement 107 the edges of the opening arrangement as well as the first sides 110 of the guiding structures 105a and 105b have been shaped. Advantageously the edge 104 of the lower part 202 of the opening arrangement is arched, so that with it a bandaging material spreading effect can be achieved. The first sides of the guiding structures are shaped so that they guide the bandaging material between the guiding structures and under them. This has been achieved by rounding or by making the first sides oblique so that the first side is at the end of the guiding structure closer to the second side 106 than at the base of the guiding structure.

FIG. 3 shows as an example a bandaging element of a first aid bandage according to the invention as seen from the side. The bandaging element is comprised of a rolled-up portion 108 and straight portion 109. The rolled-up portion is formed by bending the end of a laminar structure forming the bandaging element into an arched shape so that the first end 101 of the laminar structure is inside the rolled-up portion. Advantageously the first end of the laminar structure is not in contact with the upper surface 103 of the laminar structure. Thus the friction between the parts of the laminar structure does not hinder moving of the rolled-up portion. The rolled-up portion can be tightened by applying force essentially parallel to the rolling direction to the guiding structures. Then the rolled-up portion is rolled up further over the straight portion, whereby a part of the straight portion becomes a part of the rolled-up portion. First end 101 of the laminar structure moves inside the rolled-up portion as the rolled-up portion grows. The initial position of the rolled-up portion can be dimensioned so that as the rolling has reached its optimum position, in other words when there is a desired state of tension in the bandaging element, the first end is in contact with the bandaging material going through the opening arrangement and the bandaging material is left compressed between the different parts of the rolled-up portion. This prevents on its own part the bandaging material from loosening. The first end can be shaped, so that possible contacts with the bandaging material and the surface of the bandaging element would not impede the tightening of the rolled-up portion. There is an empty space 301 inside the rolled-up portion of the bandaging element. In a packed first aid bandage, in which there is a bandaging element according to the invention, this space can be used to store small objects to be used to use the first aid bandage or in first aid. These can include for example means used to anchor the bandage in its place, pain medication or the like.

FIG. 4 shows as an example a first aid bandage according to the invention. It is comprised of a bandaging element 400, a dressing pad 401 and bandaging material 403. The dressing pad is of a soft, absorbent, sterile and protective material or a combination of several materials to be placed against a wound or a trauma. The dressing pad in itself is prior art. The bandaging material is an elongated strip of flexible or inflexible material. It can be of textile or corresponding product. The bandaging material in itself is prior art.

The end of the bandaging material 403 is attached to the bandaging element 400. Advantageously the attachment is made underneath the bandaging element. The attachment is made so that the main part of the bandaging material is on the opposite side compared to the rolling direction of the bandaging element. The attachment of the bandaging material to the bandaging element can be made by gluing, riveting, knitting, laminating or some other corresponding method. The dressing pad 401 is attached underneath the bandaging element. The bandaging element remains between the dressing pad and the bandaging element. In the attachment of the dressing pad gluing, knitting, riveting or corresponding method can be used. To help attaching the parts to each other a support part 402 can be placed over the straight part of the bandaging element. The support part is of textile, plastic or other flexible material. Its borders extend over the edges of the straight portion of the bandaging element at least on the part of the side edges. The borders of the support element can be attached to the dressing pad or the bandaging material or both.

The size and placement of the dressing pad under the bandaging element is dimensioned advantageously so that in the optimum position of the further rolling of the rolling part or in other words when the bandaging element has been put in the desired state of tension, the rolling part of the bandaging element is approximately in the middle of the dressing pad and the bandaging element in state of tension applies also pressure to the same area.

The material of the bandaging element according to the invention has to be suitable to be used in different temperatures. The usage temperatures can vary between −30-+60° C. The material has to be also non-toxic and react with other materials as little as possible. It has to the mechanically strong enough and it has to withstand gamma sterilisation. Light weight and low thermal conductivity are also beneficial features to the material. Plastics that meet the set requirements can be used as the material, but also other materials can be possible. Also combinations of different materials can produce usable solutions.

FIGS. 5-10 show as an example a usage of a first aid bandage according to the invention. In the example of the Figures the first aid bandage is placed on a leg and two hands are used to place the bandage.

Figure 5:
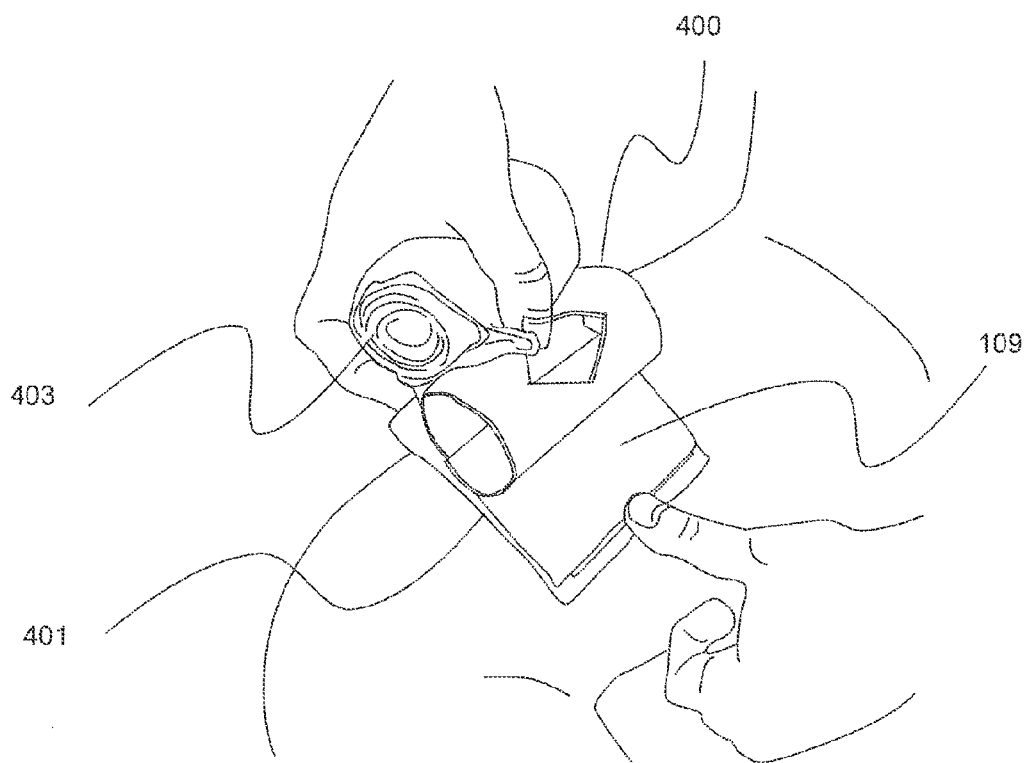

In FIG. 5 the first aid bandage is placed so that the dressing pad 401 is placed against the trauma treated. The first aid bandage is placed so that that part of the first aid band, which has the straight portion 109 of the bandaging element 400, is placed on where the compression caused by the first aid band is wanted to be applied.

Figure 6:
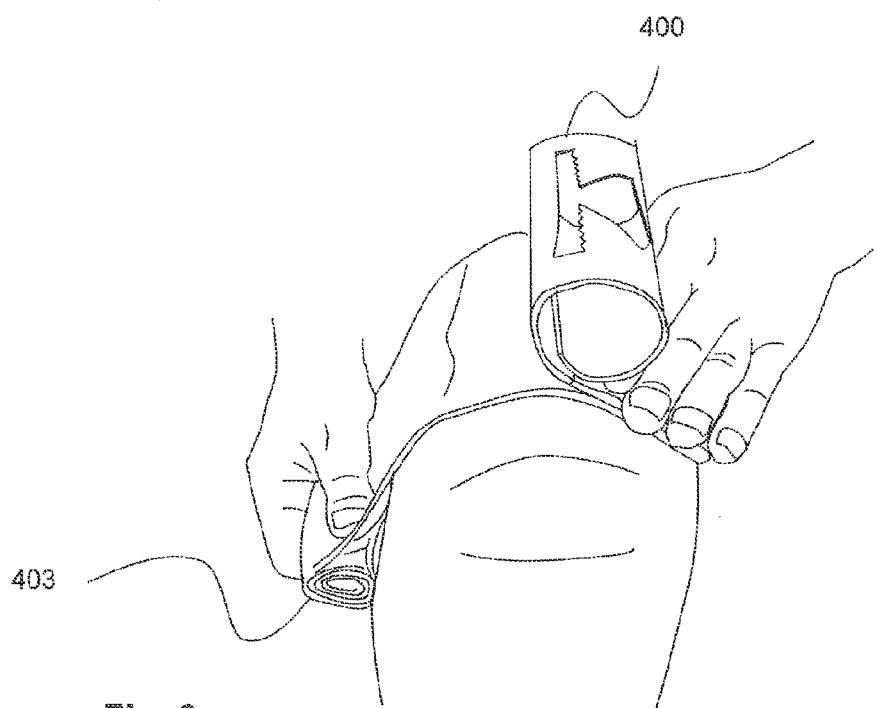

In FIG. 6 the bandaging material 403 is wound around the extremity. The bandaging material is packed in the production of the first aid bandage so that it is easy to unpack. The bandaging element 400 is held in its place so that it does not move away from its intended place.

Figure 7:
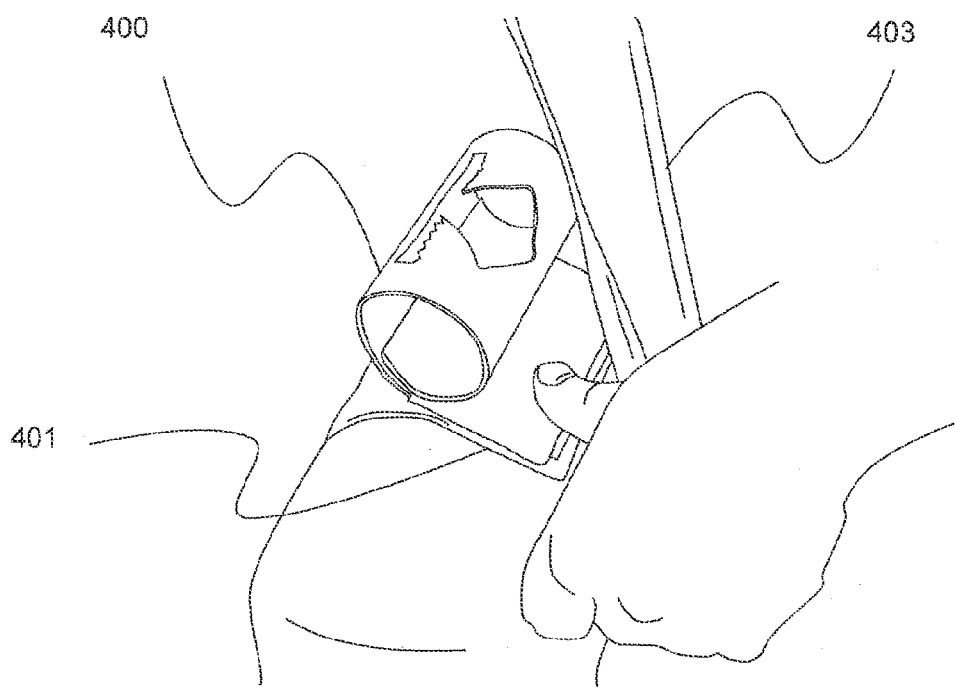

In FIG. 7 the bandaging material 403 has been brought around the extremity and it is taken towards the bandaging element 400.

Figure 8:
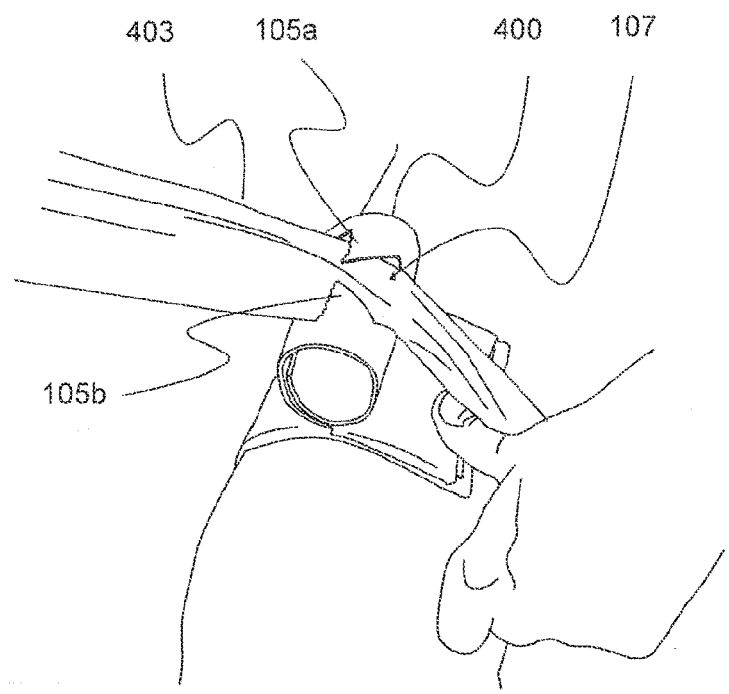

In FIG. 8 the bandaging material 403 is pulled through the opening arrangement 107 of the bandaging element 400. This is done by pressing the bandaging material over the bandaging element. Then the bandaging material is guided first to the upper part of the opening arrangement. The oblique first sides 105a and 105b of the guiding structures guide the bandaging material into the space between the guiding structures and under them. The shape of the guiding structures, in which the head parts of the guiding structures are above the level of the rolled-up portion of the bandaging element, helps the bandaging material to find its way under the guiding structures. The shaping of the edge of the lower part of the opening arrangement, which is in the described embodiment arched towards the guiding structures, spreads the bandaging material towards the sides of the opening arrangement. The bandaging material is in its place in the opening arrangement so that a part of it is under the guiding structures.

Figure 9:
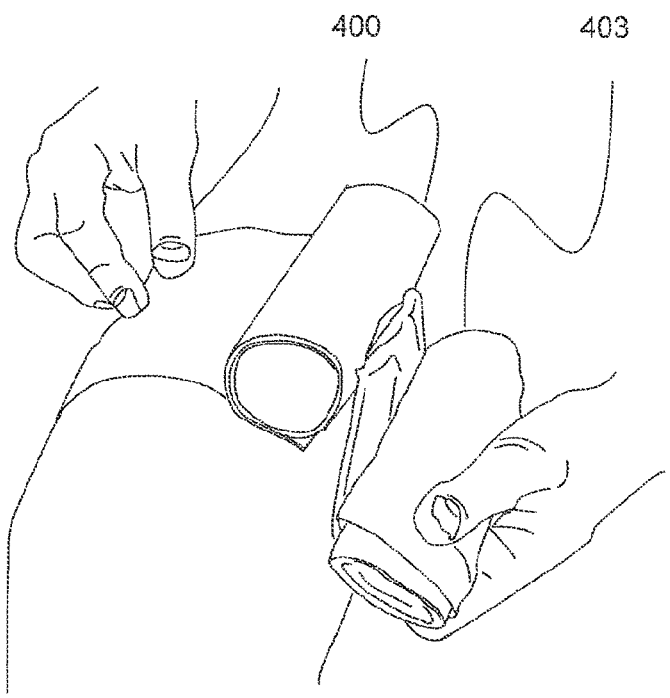

In FIG. 9 compression is caused to the first aid bandage by tightening the bandaging element 400. This is done by reversing the bandaging direction of the bandaging material 403 to the opposite, in other words towards the direction where it came from to the bandaging element. When the bandaging material is turned over the bandaging element, the shaping of the second sides of the guiding structures, which in this example is toothing, grips the bandaging material. When force, that is substantially parallel to rolling direction of the bandaging element or there is a component parallel to the rolling direction in the force applied, is applied to the bandaging material the guiding structures that have gripped the bandaging material transmit the force to the rolled-up portion of the bandaging element. If the force applied is large enough, the rolled-up portion of the bandaging element is rolled up further over the straight portion of the bandaging element. Then the rolled-up portion tends to return to its original state, in which it was before it was tightened. During the rolling the straight portion of the bandaging element changes its shape and begins then to apply pressure to the dressing pad.

Figure 10:
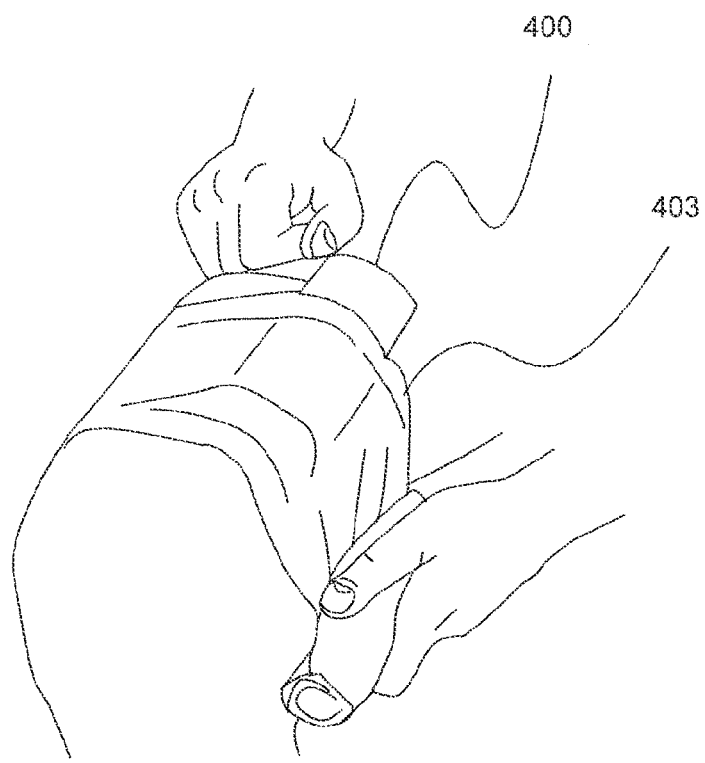

In FIG. 10 the tightened bandaging element 400 and its rolled-up portion is covered with several layers of bandaging material 403. The bandaging material is fastened to its place with some known technique. These can be tying, adhesive labels, tapes, rivets, hooks, pins and the like. The placing of the bandaging material has been made so that the state of tension in the rolled-up portion of the bandaging element has not been discharged. Since the rolled-up portion of the bandaging element tends to return to its original state, it in the same time keeps the bandaging material tight and applies pressure to the dressing pad. Then the pressure caused by the dressing pad presses on the damaged blood vessels and thus decreases the bleeding. The pressure can be regulated by the amount by which the bandaging element is tightened or in other words how much the rolled-up portion is rolled towards the rolling direction.

The first aid bandage according to the invention can be placed also in other ways than what was described in the preceding example. The first aid bandage can be placed in other extremities, body or the head. It can be placed with one hand.

In the foregoing some advantageous embodiments of the invention are described. The invention is not limited by the solutions now described, but the inventive idea can be applied in numerous ways within the limits set by the claims.

The invention claimed is:

1. A bandaging element of a first aid bandage comprising: a support part of a dressing pad and a compression part, wherein the bandaging element includes a first end and a second end, and the bandaging element is roll-shaped from the first end and a roll-shaped portion of the bandaging element is the compression part and a straight part of the bandaging element is the support part and there is an opening arrangement in the roll-shaped portion of the bandaging element for a bandaging material to go through, wherein there are one or more guiding structures in the opening arrangement for guiding the bandaging material.

2. The bandaging element of claim 1, wherein there are one or more guiding structures in the opening arrangement for guiding the bandaging material, the guiding structures include a first side and a second side, and the first side is closer to the first end of the bandaging element measured along a surface of the bandaging element than the second side.

3. The bandaging element of claim 2, wherein the second side of the guiding structure includes a shaping to grip the bandaging material.

4. The bandaging element of claim 3, wherein the shaping is a toothing.

5. The bandaging element of claim 2, wherein there are two of the guiding structures and they are substantially on opposite sides of the opening arrangement and they extend towards each other and there remains a gap between them.

6. The bandaging element of claim 2, wherein the guiding structure includes an end and a base and the guiding structure is attached to the bandaging element at the base, the first side is nearer to the second side in the end of the guiding structure than in the base of the guiding structure.

7. The bandaging element of claim 1, wherein, the roll-shaped portion of the bandaging element is configured to be rolled up over the straight part of the bandaging element to create a state of tension in the bandaging element.

8. The bandaging element of claim 1, wherein the bandaging element is plastic.

9. A first aid bandage comprising a bandaging material, a dressing pad, and a bandaging element, the dressing pad including a support part and a compression part, the dressing pad being fastened to the support part of the dressing pad and the bandaging material being fastened to the bandaging element, wherein the bandaging element includes a first end and a second end, and the bandaging element being roll-shaped from the first end, the roll-shaped portion forming the compression part, and a straight portion of the bandaging element is the support part, and the roll-shaped portion includes an opening arrangement for the bandaging material to go through and the roll-shaped portion of the bandaging element is configured to be rolled up over the straight portion of the bandaging element to create tension in the bandaging element.

10. The first aid bandage according to claim 9, wherein the bandaging material is configured to be fitted to the opening arrangement so that a part of the bandaging material is under guiding structures in the opening arrangement for guiding the bandaging material.

11. The first aid bandage according to claim 10, wherein the bandaging material in the opening arrangement of the bandaging element is arranged to catch to the guiding structures of the opening arrangement.

12. The first aid bandage according to claim 9, wherein the bandaging element is attached to an end of the bandaging material so that a main part of the bandaging material is substantially on a side of the roll-shaped portion of the bandaging element.

\* \* \* \* \*